US012314245B2

(12) United States Patent
Kurian et al.

(10) Patent No.: US 12,314,245 B2
(45) Date of Patent: May 27, 2025

(54) ARTIFICIAL INTELLIGENCE-BASED AUDITORS OF ARTIFICIAL INTELLIGENCE

(71) Applicant: Bank of America Corporation, Charlotte, NC (US)

(72) Inventors: Manu Kurian, Dallas, TX (US); Ana Maxim, Arlington, VA (US); Vinesh Patel, London (GB); Michael Young, Davidson, NC (US)

(73) Assignee: Bank of America Corporation, Charlotte, NC (US)

( * ) Notice: Subject to any disclaimer, the term of this patent is extended or adjusted under 35 U.S.C. 154(b) by 9 days.

(21) Appl. No.: 18/224,140

(22) Filed: Jul. 20, 2023

(65) Prior Publication Data

US 2025/0028704 A1   Jan. 23, 2025

(51) Int. Cl.
   *G06F 16/23*   (2019.01)
   *G16H 20/70*   (2018.01)

(52) U.S. Cl.
   CPC ......... *G06F 16/2365* (2019.01); *G16H 20/70* (2018.01)

(58) Field of Classification Search
   CPC .................... G06F 16/2365; G16H 20/70
   See application file for complete search history.

(56) References Cited

U.S. PATENT DOCUMENTS

| 2017/0315523 A1* | 11/2017 | Cross | G05B 17/02 |
| 2021/0166079 A1* | 6/2021 | Arnold | G06N 20/00 |
| 2023/0025373 A1* | 1/2023 | Kakde | G06V 10/82 |

* cited by examiner

*Primary Examiner* — Amy Ng
*Assistant Examiner* — Anthony G Gemignani
(74) *Attorney, Agent, or Firm* — Weiss & Arons LLP

(57) ABSTRACT

Systems and methods for an artificial intelligence-based auditor of artificial intelligence may be provided. The artificial-intelligence-based auditor may operate on one or more hardware processors. The artificial intelligence-based auditor may continually scan one or more operating artificial intelligence systems for productivity and operability. The scan may identify a data source powering the one or more operating artificial intelligence systems. The scan may measure a delta between an output from each of the one or more operating artificial intelligence systems. The scan may identify trends in quality of the one or more operating artificial intelligence systems. The scan may analyze instances where the one or more operating artificial intelligence systems outputted data outside of a parameter range. Based on the scan, the auditor may label each of the one or more operating artificial intelligence systems as positive, neutral or negative.

10 Claims, 8 Drawing Sheets

ARTIFICIAL INTELLIGENCE-BASED AUDITORS OF ARTIFICIAL INTELLIGENCE

FIELD OF TECHNOLOGY

Aspects of the disclosure relate to artificial intelligence.

BACKGROUND OF THE DISCLOSURE

Recently, artificial intelligence has been incorporated into a variety of computer systems. These computer systems use artificial intelligence to continually improve the processing of the computer systems.

Traditional artificial intelligence systems were supervised. Therefore, operators monitored the artificial intelligence systems to manipulate the output.

However, as artificial intelligence systems become increasingly used in a variety of commercial industries, the artificial intelligence systems are progressively becoming stand-alone computer systems with little or no supervision. The lack of supervision may cause a decrease in AI performance, productivity and/or efficiency. Therefore, it may be desirable to harness the capabilities of artificial intelligence to audit or analyze the activities executed by artificial intelligence in order to monitor artificial intelligence performance, productivity and/or efficiency.

SUMMARY OF THE DISCLOSURE

Apparatus, methods and systems for auditor artificial intelligence systems are provided. Artificial intelligence systems may be computer-operated systems that perform tasks commonly associated with humans. The auditor systems may audit artificial intelligence systems to monitor the performance of artificial intelligence systems. For the purposes of this application, artificial intelligence systems that monitor other artificial intelligence systems may be referred to as auditor artificial intelligence systems. Also, for the purposes of this application, artificial intelligence systems that may be monitored may be referred to as operating artificial intelligence systems.

Operating artificial intelligence systems may utilize a variety of sources to power and/or provide data to the artificial intelligence systems. The operating artificial intelligence systems may learn from historical data, provided by the sources, to respond to future events and/or requests.

The sources may be databases or dictionaries that include data. The sources may be open-source sources. Open-source sources may be updatable and updated by a public group. An example of an open-source source may be the internet. The sources may be closed-source sources. Closed-source sources may be updatable and updated by a private group. An example of closed-source source may be a private entity network that is only accessible to a predetermined group.

Because operating artificial intelligence may make decisions based on the sources being used to power the operating artificial intelligence, at times, operating artificial intelligence may be compared to a live object. Similar to a live object, operating artificial intelligence systems may be erratic and therefore, provide better quality responses at certain times and provide poorer quality responses at other times. Therefore, an auditor artificial intelligence system may identify the source in order to classify an outcome provided by the operating artificial intelligence system. Furthermore, trends in operating artificial intelligence quality may be identified to classify the outcomes provided by operating artificial intelligence.

At times, an operating artificial intelligence system may manipulate an outcome based on one or more biases. Therefore, an auditor artificial intelligence system may audit outputs from multiple operating artificial intelligence systems within the same environment. The deltas between the outputs may identify whether an operating artificial intelligence system produces manipulative outputs that are based on one or more biases.

Additionally, auditor artificial intelligence systems may study and analyze instances where operating artificial intelligence systems output data outside of a parameter range. Many times, an operating artificial intelligence system may be provided with a parameter range that determines a plot for output. If the operating artificial intelligence system produced an output outside of a parameter range, the auditor artificial intelligence may inspect the cause of such an output.

Auditor artificial intelligence systems may work in a team. As such, multiple auditor artificial intelligence systems may operate in tandem. Each of the artificial intelligence systems may, or may not, be aware of the other auditor artificial intelligence systems. Each of the auditor artificial intelligence systems may use the same or different auditing techniques. The combination of the results of the auditor artificial intelligence systems may be used to label an operating artificial intelligence system with a positive, negative or neutral label.

Various scales may be used to label an operating artificial intelligence system. The scales may include a number scale, in which a completely negative operating artificial intelligence system may be identified as $-1$, a completely positive operating artificial intelligence system may be identified as 1 and a completely neutral operating artificial intelligence system may be identified as 0. The scales may also include a decimal scale, in which a decimal number between $-1$ (negative) and 1 (positive), is used to label the operating artificial intelligence system. An example of a decimal number may be 0.65 or $-0.02$.

The label may be used to enable communication with the operating artificial intelligence system. As such, the auditor artificial intelligence system may operate for an entity. The entity may want to ensure that its sub-entities are communicating with positive or neutral operating artificial intelligence systems. Therefore, the auditor artificial intelligence systems may halt communications with operating artificial intelligence systems labeled as negative, monitor communications with operating artificial intelligence systems labeled as neutral and enable communications with operating artificial intelligence systems labeled as positive.

BRIEF DESCRIPTION OF THE DRAWINGS

The objects and advantages of the invention will be apparent upon consideration of the following detailed description, taken in conjunction with the accompanying drawings, in which like reference characters refer to like parts throughout, and in which.

DETAILED DESCRIPTION OF THE DISCLOSURE

Figure 1:
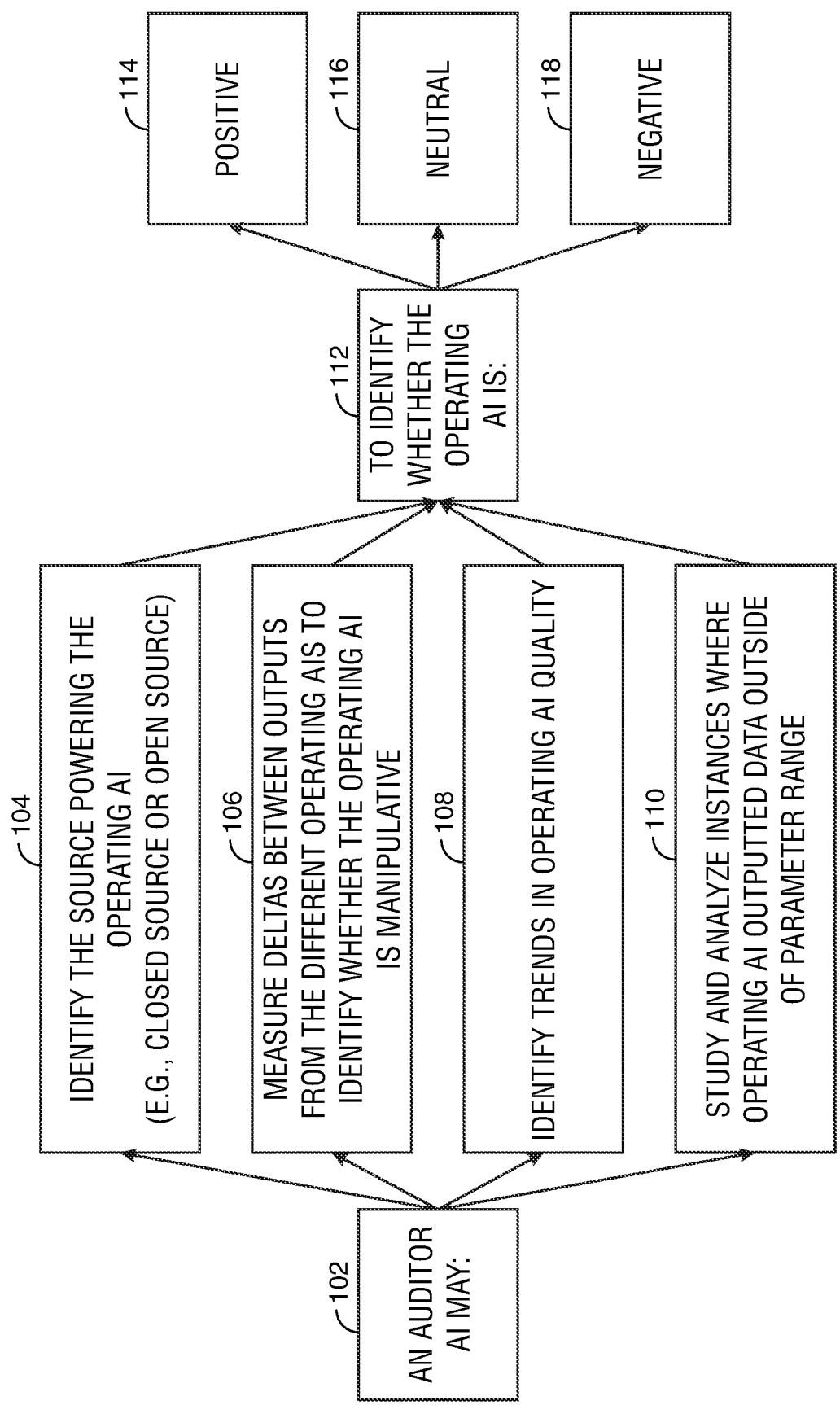
FIG. 1 shows an illustrative diagram in accordance with principles of the disclosure.

Apparatus, methods and systems for auditing artificial intelligence-based systems is provided. Methods may include continually scanning, by a level one artificial intelligence-based auditor, an operating artificial intelligence system for productivity and operability. Methods may include outputting, by the level one artificial intelligence-based auditor, a first productivity and operability score for the operating artificial intelligence system.

Methods may include continually scanning, by a level two artificial intelligence-based auditor, the one or more operating artificial intelligence systems for productivity and operability. Methods may include outputting, by the level two artificial intelligence-based auditor, a second productivity and operability score for the operating artificial intelligence system.

Methods may include continually scanning, by a level three artificial intelligence-based auditor, the one or more operating artificial intelligence systems for productivity and operability. Methods may include outputting, by the level three artificial intelligence-based auditor, a third productivity and operability score for the operating artificial intelligence system.

Methods may include continually scanning, by a level four artificial intelligence-based auditor, the one or more operating artificial intelligence systems for productivity and operability. Methods may include outputting, by the level four artificial intelligence-based auditor, a fourth productivity and operability score for the operating artificial intelligence system.

Methods may include grouping, by an artificial intelligence-based syndicator, the first productivity and operability score, the second productivity and operability score, the third productivity and operability score and the fourth productivity and operability score into a productivity and operability score grouping. Methods may include identifying an outlier within the productivity and operability score grouping, the outlier being one of the first productivity and operability score, the second productivity and operability score, the third productivity and operability score or the fourth productivity and operability score. Methods may include removing the outlier from the grouping. Methods may include outputting a syndicated productivity and operability score, the syndicated productivity and operability score including a combination of the productivity and operability scores included within the grouping. Methods may include labeling, by an artificial intelligence-based labeler, the operating artificial intelligence system as positive, neutral or negative based on the syndicated productivity and operability score.

The level one auditor may operate independently from the level two, level three and level four auditors. The level two auditor may operate independently from the level one, level three and level four auditors. The level three auditor may operate independently from the level one, level two and level four auditors. The level four auditor may operate independently from the level one, level two and level three auditors.

An artificial intelligence-based auditor of artificial intelligence may also be provided. The artificial intelligence-based auditor may operate on one or more hardware processors. The artificial intelligence-based auditor may be operable to continually scan one or more operating artificial intelligence systems for productivity and operability.

The continual scanning may include identifying a data source powering the one or more operating artificial intelligence systems. The data source may be an open-source data source. Examples of an open-source data source may be publicly available data on a publicly available network. The data source may be a closed-source data source. Examples of a closed-source data source may data available only within a private network.

The continual scanning may also include measuring a delta between an output from each of the one or more operating artificial intelligence systems. The delta between the output from each of the one or more operating artificial intelligence systems may identify an anomalous operating artificial intelligence system.

The continual scanning may also include identifying trends in qualify of the one or more operating artificial intelligence systems. The trends may relate to artificial security clearance level, artificial intelligence skill level and artificial intelligence intent. Artificial security clearance level may include a metric corresponding to a quantity of personal, classified or confidential information included in the outputs of the artificial intelligence system. Artificial intelligence skill level may include a metric corresponding to the accuracy of the outputs of the artificial intelligence system as it correlates to a query of the artificial intelligence system. Artificial intelligence intent may include a metric corresponding to an identified intent of the artificial intelligence system. Examples of intents may include positive intents, negative intents, biased intents, non-biased intents or any other suitable intents. The metric may correlate the output of the artificial intelligence system to an identified intent.

The trends may also relate to a sophistication degree, an empathy degree, an emotional capacity degree, a creativity degree and/or a thought capacity degree.

A sophistication degree may be based on the quality and level of the language used by the artificial intelligence system. The sophistication degree may also be based on the ability of the artificial intelligence system to utilize historical data to generate new data and information.

An empathy degree may be based on the ability of the artificial intelligence system to consider viewpoints of a receiver of the output.

An emotional capacity degree may be based on the ability of artificial intelligence system to consider sentiment in producing the output.

A creativity degree may be based on the ability of the artificial intelligence system to produce and/or generate new outputs.

A thought capacity degree may be based on the ability of the artificial intelligence system to combine various elements of information to generate an output.

The continual scanning may also include analyzing instances where the one or more operating artificial intelligence systems output data outside of a parameter range.

Based on the scan, the artificial intelligence-based auditor may identify each of the one or more operating artificial intelligence systems as positive, negative or neutral. When the operating artificial intelligence system is identified and/or labeled as positive, the artificial intelligence-based auditor may enable communications between an entity with which the artificial intelligence-based auditor is associated and the operating artificial intelligence system. When the operating artificial intelligence system is identified and/or labeled as neutral, the artificial intelligence-based auditor may monitor communications between an entity with which the artificial intelligence-based auditor is associated and the operating artificial intelligence system. When the operating artificial intelligence system is identified and/or labeled as negative, the artificial intelligence-based auditor may block communications between an entity with which the artificial intelligence-based auditor is associated and the operating artificial intelligence system.

Examples of an entity with which the artificial intelligence-based auditor is associated may include a computing server, business entity, a financial entity or any other suitable entity. As such, enabling communications between the entity and the operating artificial intelligence system may include enabling emails, chats, phone calls and other suitable communications to be received from and/or transmitted to the operating artificial intelligence system.

Apparatus and methods described herein are illustrative. Apparatus and methods in accordance with this disclosure will now be described in connection with the figures, which form a part hereof. The figures show illustrative features of apparatus and method steps in accordance with the principles of this disclosure. It is to be understood that other embodiments may be utilized and that structural, functional and procedural modifications may be made without departing from the scope and spirit of the present disclosure.

The steps of methods may be performed in an order other than the order shown or described herein. Embodiments may omit steps shown or described in connection with illustrative methods. Embodiments may include steps that are neither shown nor described in connection with illustrative methods.

Illustrative method steps may be combined. For example, an illustrative method may include steps shown in connection with another illustrative method.

Apparatus may omit features shown or described in connection with illustrative apparatus. Embodiments may include features that are neither shown nor described in connection with the illustrative apparatus. Features of illustrative apparatus may be combined. For example, an illustrative embodiment may include features shown in connection with another illustrative embodiment.

FIG. 1 shows an illustrative flow chart. The illustrative flow chart shows an auditor artificial intelligence ("AI") auditing an operating AI system.

Step 102 shows that an auditor AI may be used to audit an operating AI system. The auditor AI may execute steps 104, 106, 108 and 110. Each of steps 104, 106, 108 and 110 may be used to identify whether the operating AI can be labeled, as shown at 112, as positive, shown at 114, neutral, shown at 116 or negative, shown at 118.

Step 104 shows identifying the source powering the operating AI. The source may be a database or dictionary used to provide the AI with data. The source may be a closed source, such as a private dictionary, or private entity data. The source may be an open source, such as data provided on the internet. The source may be continually, or continuously updated. As such, the AI may be continuously changing.

Step 104 shows measuring deltas between outputs. When multiple operating AIs are used for the same endeavor, comparing the outputs of the multiple AIs may be useful to identify an outlier and determine whether one or more of the operating AIs are manipulative or biased in some way.

Step 108 shows identifying trends in operating AI quality. Because AIs are continuously changing, operating AIs may trend in their outputs. As such, trends in outputs of operating AIs may be useful to identify whether the quality of an AI is increasing or decreasing.

Step 110 shows study and analyzing instances whether operating AIs output data outside of a parameter range. Various parameter ranges may be defined for an operating AI. When an AI attempts to provide output outside of that parameter range, it may serve as a signal that AI may be executing in a manipulative fashion or may be attempting to control a specific system.

It should be noted that each of steps 104, 106, 108 and 110 may be weighted evenly when labeling the AI as positive, neutral or negative. In certain embodiments, each of steps 104, 106, 108 and 110 may be weighted unevenly when labeling the AI as positive, neutral or negative. As such, certain steps may be given more priority than other steps.

Figure 2:
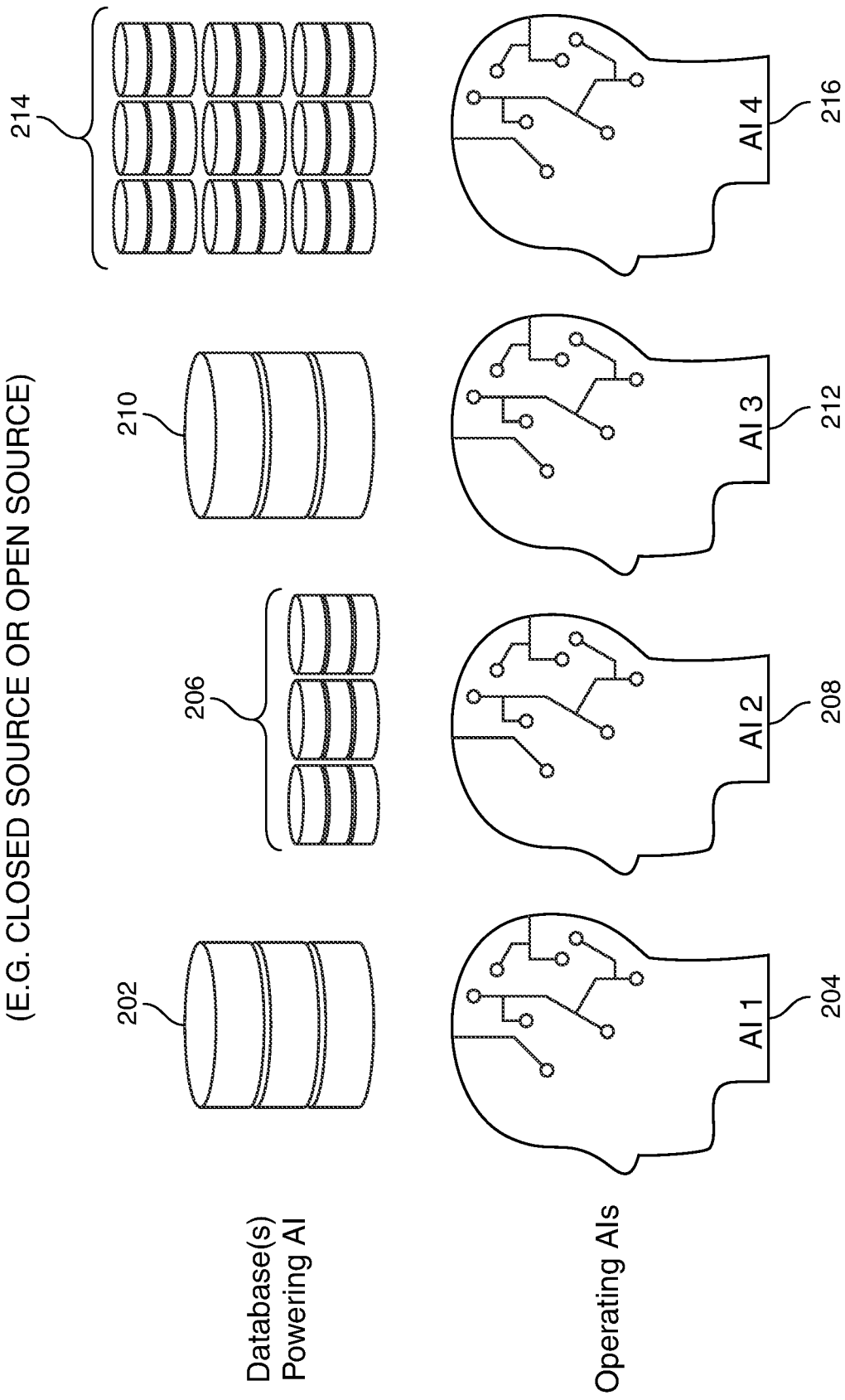
FIG. 2 shows another illustrative diagram in accordance with principles of the disclosure.

FIG. 2 shows an illustrative diagram. The illustrative diagram shows operating AIs, as shown at 204, 208, 212 and 216 and the databases powering the illustrative AIs, as shown at 202, 206, 210 and 214. Each of the operating AIs may produce output based on the information being fed from the database powering the AI. As such, each AI may produce different outputs to the same set of circumstances.

Figure 3:
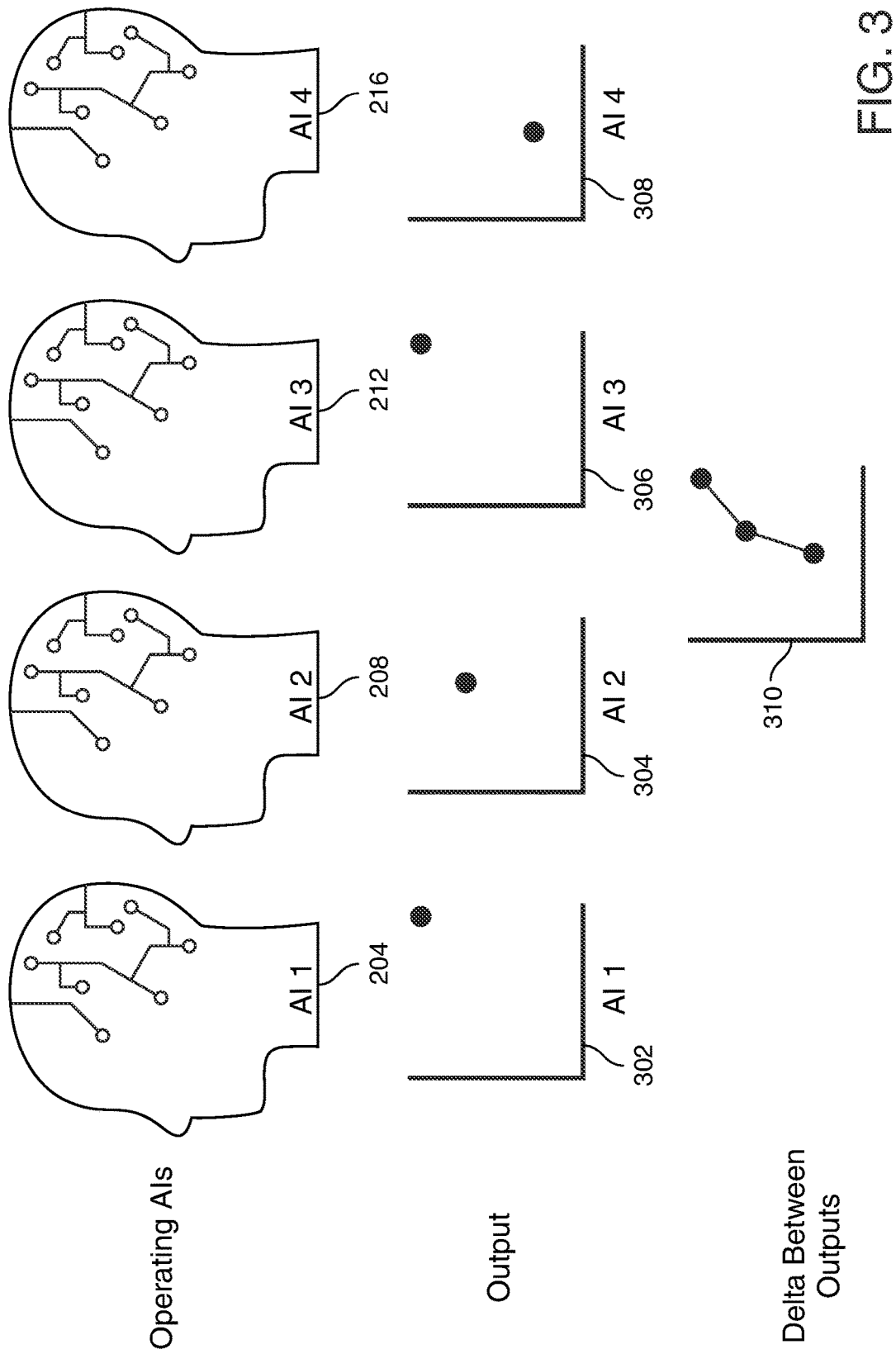
FIG. 3 shows still another illustrative diagram in accordance with principles of the disclosure.

FIG. 3 shows another illustrative diagram. The illustrative diagram shows measuring deltas between outputs from different operating AIs. The deltas may be used to identify whether the operating AI is manipulative, which may be used to label a negative AI. Operating AIs may be shown at 204, 208, 212 and 216. Outputs from each of the operating AIs may be shown at 302, 304, 306 and 308. Deltas between outputs may be shown at 310. The trend line shown on the delta graph 310 may be used as a baseline to identify which operating AIs are producing output within the baseline, at the edge of the baseline or outside the baseline.

Figure 4:
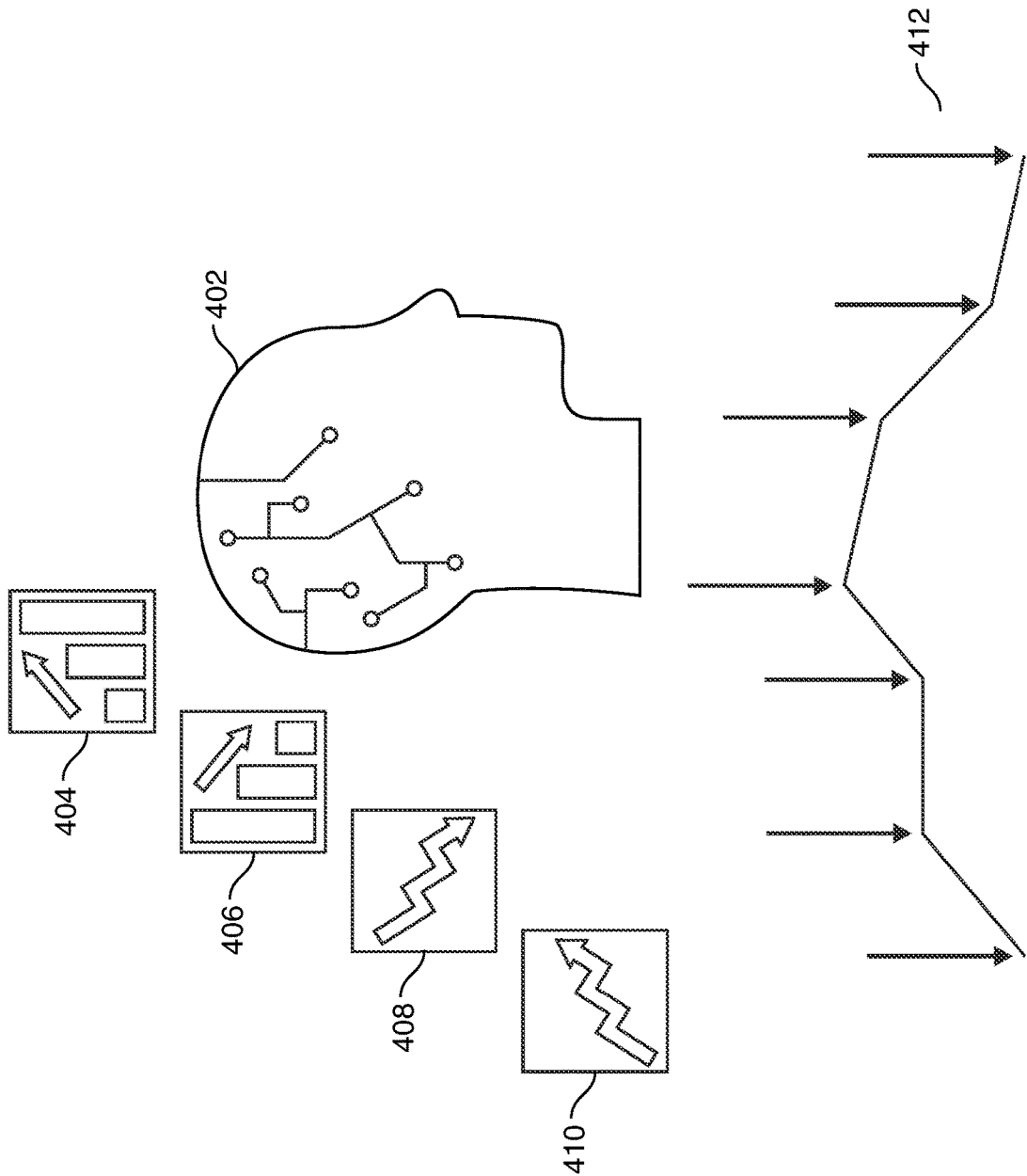
FIG. 4 shows yet another illustrative diagram in accordance with principles of the disclosure.

FIG. 4 shows another illustrative diagram. The illustrative diagram shows identifying trends in operating AI quality. An operating AI is shown at 402. The operating AI may produce various outputs. Each output may be identified as a positive output, neutral output or a negative output. Each output may categorize the trend of the operating AI.

A trendline may be shown at 412. Each arrow may represent an output of the operating AI. The trendline may show that operating AI may be stable based on the most recent seven outputs. The trendline may also represent a segment of time. For example, the trendline may represent an hour and each arrow may represent a portion of the hour, such as, for example, ten minutes.

Various other trendlines are shown at 404, 406, 408 and 410. Each of these trendlines may be based on a plurality of outputs produced by operating AI 402.

Figure 5:
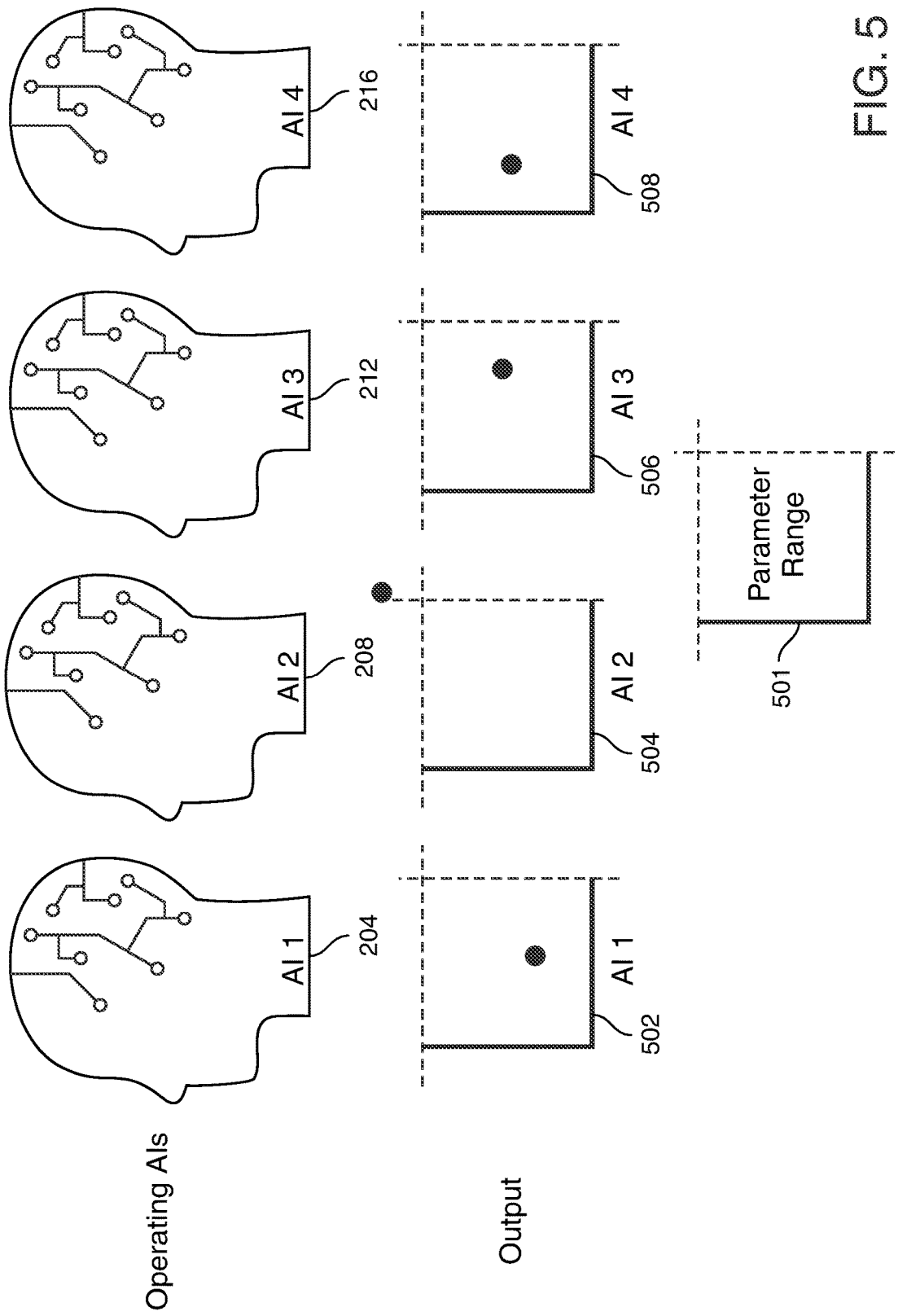
FIG. 5 shows still yet another illustrative diagram in accordance with principles of the disclosure.

FIG. 5 shows an illustrative diagram. The illustrative diagram shows studying and analyzing instances where operating AIs output data outside of a parameter range. Operating AIs may be shown at 204, 208, 212 and 216. The parameter range may be shown at 501. The outputs of each of the operating AIs as compared to the parameter range may be shown at 502, 504, 506 and 508. As shown at output 504, AI 2 may produce output outside of a parameter range. The cause for this output may be identified in order to determine whether AI 2 is positive, neutral or negative.

Figure 6:
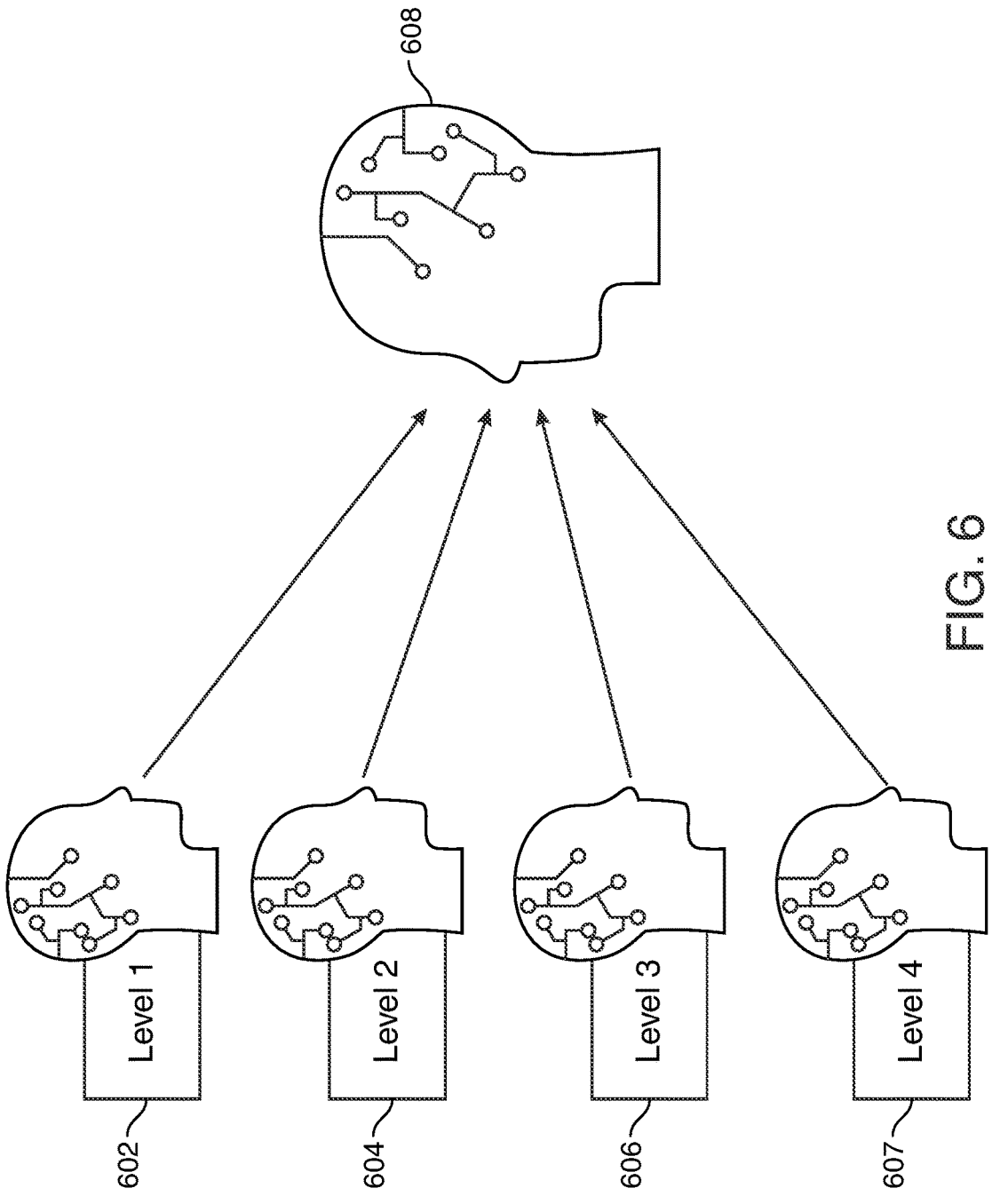
FIG. 6 shows an illustrative flow chart in accordance with principles of the disclosure.

FIG. 6 shows another illustrative diagram. The illustrative diagram shows using independent artificial intelligence auditors as a team. The team may include a level 1 auditor, shown at 602, a level 2 auditor, shown at 604, a level 3 auditor, shown at 606 and a level 4 auditor, shown at 607. Each of level 1, level 2, level 3 and level 4 auditors may audit operating AI 608.

Each of level 1, level 2, level 3 and level 4 auditors may utilize a different method to analyze operating AI 608. Each of level 1, level 2, level 3 and level 4 auditors may utilize the same method to analyze operating AI 608. In some embodiments, each of level 1, level 2, level 3 and level 4 may be aware of each other and work together. In other embodiments, each of level 1, level 2, level 3 and level 4 may not be aware of each other. As such, a separate syndicator may be used to combine the results of the level 1, level 2, level 3 and level 4 auditors.

Figure 7:
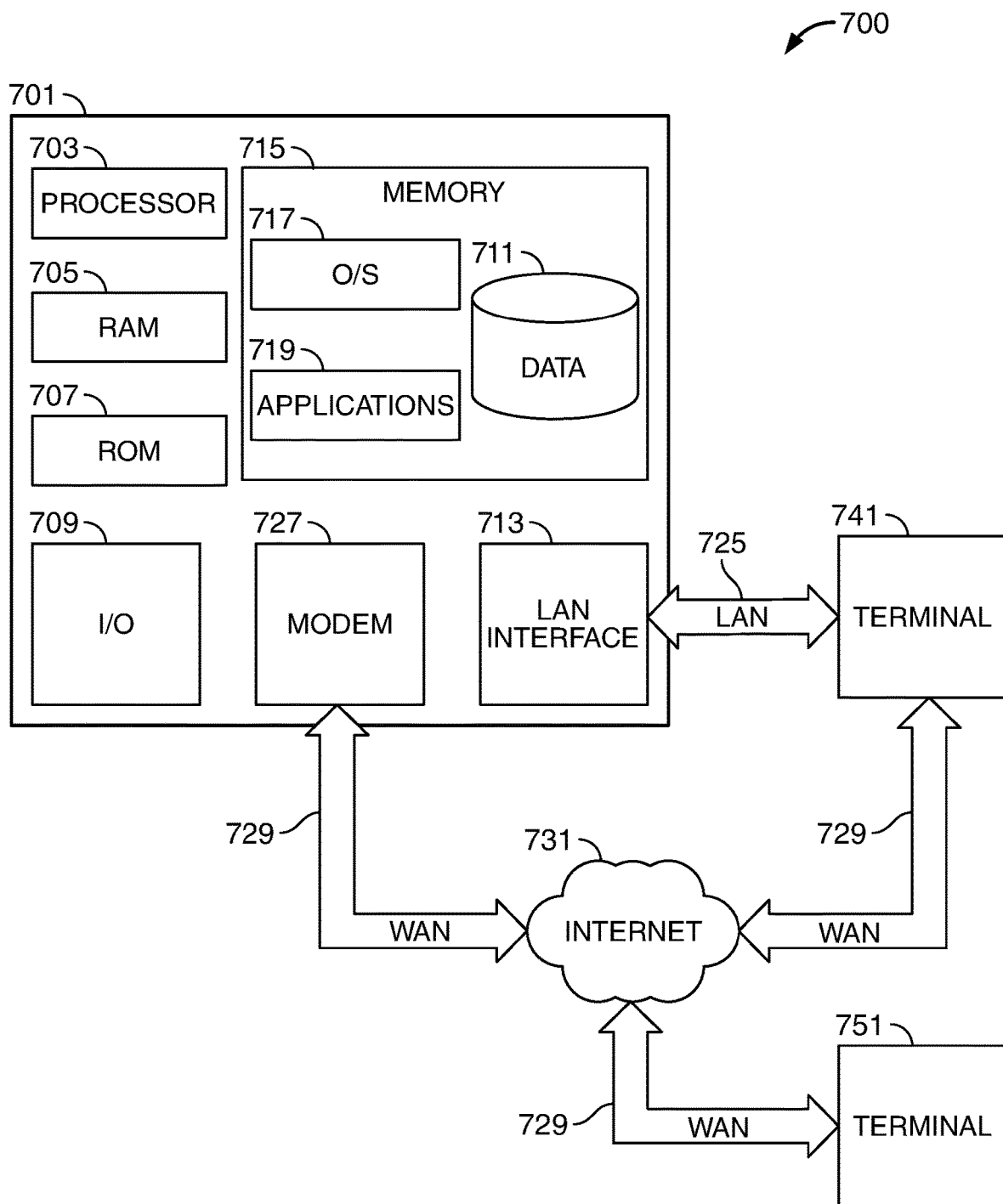
FIG. 7 shows another illustrative diagram in accordance with principles of the disclosure.

FIG. 7 shows an illustrative block diagram of system 700 that includes computer 701. Computer 701 may alternatively be referred to herein as a "server" or a "computing device." Computer 701 may be a workstation, desktop, laptop, tablet, smart phone, or any other suitable computing device. Elements of system 700, including computer 701, may be used to implement various aspects of the systems and methods disclosed herein.

Computer 701 may have a processor 703 for controlling the operation of the device and its associated components, and may include RAM 705, ROM 707, input/output module 709, and a memory 715. The processor 703 may also execute all software running on the computer—e.g., the operating system and/or voice recognition software. Other components commonly used for computers, such as EEPROM or Flash memory or any other suitable components, may also be part of the computer 701.

The memory 715 may comprise any suitable permanent storage technology—e.g., a hard drive. The memory 715 may store software including the operating system 717 and application(s) 719 along with any data 711 needed for the operation of the system 700. Memory 715 may also store videos, text, and/or audio assistance files. The videos, text, and/or audio assistance files may also be stored in cache memory, or any other suitable memory. Alternatively, some or all of computer executable instructions (alternatively referred to as "code") may be embodied in hardware or firmware (not shown). The computer 701 may execute the instructions embodied by the software to perform various functions.

Input/output ("I/O") module may include connectivity to a microphone, keyboard, touch screen, mouse, and/or stylus through which a user of computer 701 may provide input. The input may include input relating to cursor movement. The input may relate to transaction pattern tracking and prediction. The input/output module may also include one or more speakers for providing audio output and a video display device for providing textual, audio, audiovisual, and/or graphical output. The input and output may be related to computer application functionality. The input and output may be related to transaction pattern tracking and prediction.

System 700 may be connected to other systems via a local area network (LAN) interface 713.

System 700 may operate in a networked environment supporting connections to one or more remote computers, such as terminals 741 and 751. Terminals 741 and 751 may be personal computers or servers that include many or all of the elements described above relative to system 700. The network connections depicted in FIG. 7 include a local area network (LAN) 725 and a wide area network (WAN) 729, but may also include other networks. When used in a LAN networking environment, computer 701 is connected to LAN 725 through a LAN interface or adapter 713. When used in a WAN networking environment, computer 701 may include a modem 727 or other means for establishing communications over WAN 729, such as Internet 731.

It will be appreciated that the network connections shown are illustrative and other means of establishing a communications link between computers may be used. The existence of various well-known protocols such as TCP/IP, Ethernet, FTP, HTTP and the like is presumed, and the system can be operated in a client-server configuration to permit a user to retrieve web pages from a web-based server. The web-based server may transmit data to any other suitable computer system. The web-based server may also send computer-readable instructions, together with the data, to any suitable computer system. The computer-readable instructions may be to store the data in cache memory, the hard drive, secondary memory, or any other suitable memory.

Additionally, application program(s) 719, which may be used by computer 701, may include computer executable instructions for invoking user functionality related to communication, such as e-mail, Short Message Service (SMS), and voice input and speech recognition applications. Application program(s) 719 (which may be alternatively referred to herein as "plugins," "applications," or "apps") may include computer executable instructions for invoking user functionality related to performing various tasks. The various tasks may be related to transaction pattern tracking and prediction.

Computer 701 and/or terminals 741 and 751 may also be devices including various other components, such as a battery, speaker, and/or antennas (not shown).

Terminal 751 and/or terminal 741 may be portable devices such as a laptop, cell phone, Blackberry™, tablet, smartphone, or any other suitable device for receiving, storing, transmitting and/or displaying relevant information. Terminals 751 and/or terminal 741 may be other devices. These devices may be identical to system 700 or different. The differences may be related to hardware components and/or software components.

Any information described above in connection with database 711, and any other suitable information, may be stored in memory 715. One or more of applications 719 may include one or more algorithms that may be used to implement features of the disclosure, and/or any other suitable tasks.

The invention may be operational with numerous other general purpose or special purpose computing system environments or configurations. Examples of well-known computing systems, environments, and/or configurations that may be suitable for use with the invention include, but are not limited to, personal computers, server computers, hand-held or laptop devices, tablets, mobile phones, smart phones and/or other personal digital assistants ("PDAs"), multiprocessor systems, microprocessor-based systems, set top boxes, programmable consumer electronics, network PCs, minicomputers, mainframe computers, distributed computing environments that include any of the above systems or devices, and the like.

The invention may be described in the general context of computer-executable instructions, such as program modules, being executed by a computer. Generally, program modules include routines, programs, objects, components, data structures, etc., that perform particular tasks or implement particular abstract data types. The invention may also be practiced in distributed computing environments where tasks are performed by remote processing devices that are linked through a communications network. In a distributed computing environment, program modules may be located in both local and remote computer storage media including memory storage devices.

Figure 8:
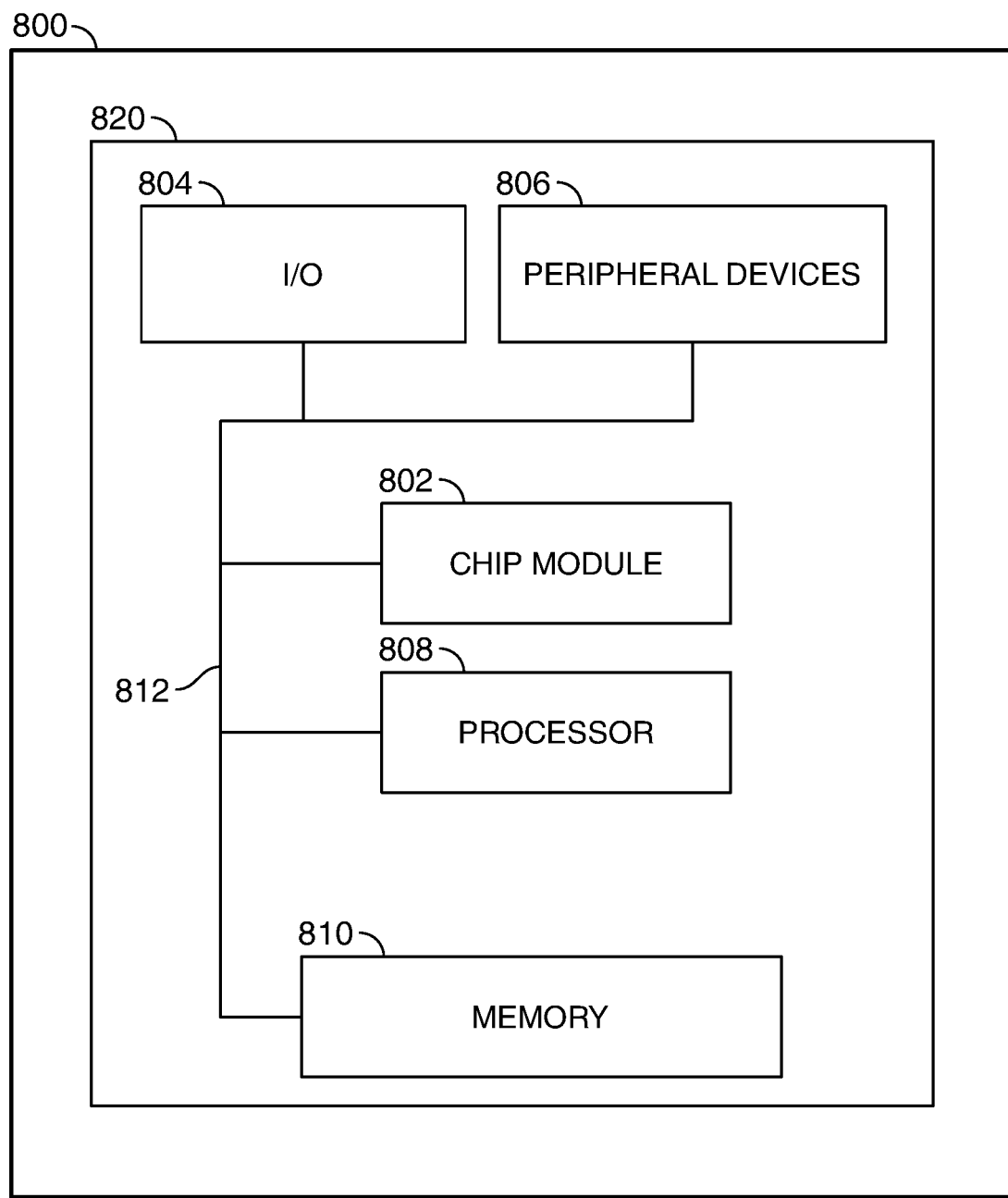
FIG. 8 shows yet another illustrative diagram in accordance with principles of the disclosure.

FIG. 8 shows illustrative apparatus 800 that may be configured in accordance with the principles of the disclosure. Apparatus 800 may be a computing machine. Apparatus 800 may include one or more features of the apparatus shown in FIG. 7. Apparatus 800 may include chip module 802, which may include one or more integrated circuits, and which may include logic configured to perform any other suitable logical operations.

Apparatus 800 may include one or more of the following components: I/O circuitry 804, which may include a transmitter device and a receiver device and may interface with fiber optic cable, coaxial cable, telephone lines, wireless devices, PHY layer hardware, a keypad/display control device or any other suitable media or devices; peripheral devices 806, which may include counter timers, real-time timers, power-on reset generators or any other suitable peripheral devices; logical processing device 808, which may compute data structural information and structural parameters of the data; and machine-readable memory 810.

Machine-readable memory 810 may be configured to store in machine-readable data structures: machine executable instructions (which may be alternatively referred to herein as "computer instructions" or "computer code"), applications, signals, and/or any other suitable information or data structures.

Components 802, 804, 806, 808 and 810 may be coupled together by a system bus or other interconnections 812 and may be present on one or more circuit boards such as 820. In some embodiments, the components may be integrated into a single chip. The chip may be silicon-based.

Thus, systems and methods for artificial intelligence-based auditors of artificial intelligence are provided. Persons skilled in the art will appreciate that the present invention can be practiced by other than the described embodiments, which are presented for purposes of illustration rather than of limitation. The present invention is limited only by the claims that follow.

What is claimed is:

1. An artificial intelligence-based auditor operating to gatekeep electronic communications between an entity and a plurality of operating artificial intelligence systems, the artificial-intelligence-based auditor operating on one or more hardware processors within the entity, the artificial intelligence-based auditor operable to:
    gatekeep electronic communications transmitted between a plurality of computing nodes operating within the entity and a plurality of operating artificial intelligence systems operating external to the entity, said plurality of operating artificial intelligence systems operable to generate output, said gatekeep by:
        execution of a continual productivity and operability scan on:
            each operating artificial intelligence system included in the plurality of operating artificial intelligence systems; and
            the output generated by each operating artificial intelligence system;
        the continual productivity and operability scan comprising:
            identification of a data source powering the artificial intelligence system;
            identification of a plurality of quality metrics of the operating artificial intelligence system, each of the plurality of quality metrics expressed as a trendline across a timeframe, the plurality of quality metrics comprising:
                an artificial security clearance metric corresponding to a quantity of personal, classified or confidential information included in the output of the operating artificial intelligence system;
                an artificial intelligence skill metric corresponding to an accuracy of the output of the operating artificial intelligence system as the output of the operating artificial intelligence system correlates to a query of the operating artificial intelligence system;
                an artificial intelligence intent metric corresponding to a correlation between an identified intent and the output of the operating artificial intelligence system;
                a sophistication metric based on:
                    a quality of language included in the output of the operating artificial intelligence system;
                    a level of language included in the output of the operating artificial intelligence system; and
                    an ability of the operating artificial intelligence system to harness historical data to generate new information, said new information included in the output;
                an empathy metric based on an ability of the operating artificial intelligence system to consider viewpoints of a receiver of the output;
                an emotional capacity metric based on an ability of the operating artificial intelligence system to consider sentiment in generating the output; and
                a thought capacity metric based on an ability of the operating artificial intelligence system to combine various elements to generate the output; and
            identification of one or more instances when the output of the operating artificial intelligence system plotted outside of a parameter range;
        for each operating artificial intelligence system, syndication of a result of the continual productivity and operability scan into a syndicated productivity and operability score;
        measurement of a delta between the syndicated productivity and operability scores assigned to each operating artificial intelligence system included in the plurality of operating artificial intelligence system and a remainder of the syndicated productivity and operability scores assigned to the plurality of operating artificial intelligence systems;
        label a first operating artificial intelligence system included in the plurality operating artificial intelligence systems as manipulative when the measurement of the delta indicates that the output generated by the first operating artificial intelligence system is an outlier;
    wherein when the first operating artificial intelligence system is labeled manipulative:
        block receipt of a first subset of the electronic communications at the plurality of computing nodes, said first subset of the electronic communications transmitted from the first operating artificial intelligence systems to one or more computing nodes included in the plurality of computing nodes, said first subset of the electronic communications comprising emails, chats and telephone calls; and block transmission of a second subset of the electronic communications at the plurality of computing nodes, said second subset of the electronic communications transmitted from a node included the plurality of computing nodes to the first operating artificial intelligence system.

2. The artificial intelligence-based auditor of claim 1 wherein the data source is identified as an open-source data source.

3. The artificial intelligence-based auditor of claim 1 wherein the data source is identified as a closed-source data source.

4. The artificial intelligence-based auditor of claim 1 wherein the artificial intelligence-based auditor:
labels a second operating artificial intelligence system included in the plurality of operating artificial intelligence systems as positive when the measurement of the delta indicates that the output generated by the second operating artificial intelligence system is within a baseline range of the output generated by the plurality of operating artificial intelligence systems; and
enables:
receipt of communications at the plurality of computing nodes, from with the second operating artificial intelligence system; and
transmission of communications from the plurality computing nodes to the second operating artificial intelligence system.

5. The artificial intelligence-based auditor of claim 1 wherein the artificial intelligence-based auditor:
labels a second operating artificial intelligence system included in the plurality of operating artificial intelligence systems as neutral when the measurement of the delta indicates that an output generated by the second operating artificial intelligence system is at the edge of a baseline range of the output generated by the plurality of operating artificial intelligence systems; and
monitors communications between the plurality of computing nodes and the second operating artificial intelligence system.

6. A method for auditing an operating artificial intelligence system, the operating artificial intelligence system executing on one or more hardware processors, method comprising:
gatekeeping electronic communications transmitted between a plurality of computing nodes operating within an entity and a plurality of operating artificial intelligence systems operating external to the entity, said plurality of operating artificial intelligence systems operable to generate output, said gatekeeping comprising:
continually executing a productivity and operability scan on each operating artificial intelligence system included in the plurality of operating artificial intelligence systems and the output generated by each operating artificial intelligence system included in the plurality of artificial intelligence system, said continual productivity and operability scan comprising:
identifying a data source powering the operating artificial intelligence system;
identifying a plurality of quality metrics of the operating artificial intelligence system, each of the plurality of quality metrics expressed as a trendline across a timeframe, the plurality of quality metrics comprising:
an artificial security clearance metric corresponding to a quantity of personal, classified or confidential information included in the output of the operating artificial intelligence system;
an artificial intelligence skill metric corresponding to an accuracy of the output of the operating artificial intelligence system as the output of the operating artificial intelligence system correlates to a query of the operating artificial intelligence system;
an artificial intelligence intent metric corresponding to a correlation between an identified intent and the output of the operating artificial intelligence system;
a sophistication metric based on:
a quality of language included in the output of the operating artificial intelligence system;
a level of language included in the output of the operating artificial intelligence system; and
an ability of the operating artificial intelligence system to harness historical data to generate new information, said new information included in the output;
an empathy metric based on an ability of the operating artificial intelligence system to consider viewpoints of a receiver of the output;
an emotional capacity metric based on an ability of the operating artificial intelligence system to consider sentiment in generating the output; and
a thought capacity metric based on an ability of the operating artificial intelligence system to combine various elements to generate the output;
identifying one or more instances when the output of the operating artificial intelligence system plotted outside of a parameter range;
syndicating a result of the continual productivity and operability scan into a syndicated productivity and operability score for each operating artificial intelligence system included in the plurality of operating artificial intelligence systems;
measuring a delta between the syndicated productivity and operability score assigned to each operating artificial intelligence system included in the plurality of operating artificial intelligence systems and a remainder of the syndicated productivity and operability scores assigned to the plurality of operating artificial intelligence systems;
labeling a first operating artificial intelligence system included in the plurality of operating artificial intelligence systems as manipulative when the measuring the delta indicates that the output generated by the first operating artificial intelligence system is an outlier; and
wherein when the first operating artificial intelligence system is labeled manipulative:
blocking electronic communication traffic between the plurality of computing nodes and the first operating artificial intelligence system.

7. The method of claim 6 wherein the data source is identified as an open-source data source.

8. The method of claim 6 wherein the data source is identified as a closed-source data source.

9. The method of claim 6 further comprising:
labeling a second operating artificial intelligence system included in the plurality of artificial intelligence systems as positive when the measuring the delta indicates that the output generated by the second operating artificial intelligence system is within a baseline range of the output generated by the plurality of operating artificial intelligence systems; and enabling electronic communication traffic between the plurality of computing nodes and the second operating artificial intelligence system.

10. The method of claim 6 further comprising:

labeling a second operating artificial intelligence system included in the plurality of artificial intelligence systems as neutral when the measuring the delta indicates that the output generated by the second operating artificial intelligence system is at the edge of a baseline range of the output generated by the plurality of operating artificial intelligence systems; and monitoring electronic communication traffic between the plurality of nodes and the second operating artificial intelligence system.

* * * * *